United States Patent [19]

Higuchi et al.

[11] Patent Number: 4,874,542
[45] Date of Patent: Oct. 17, 1989

[54] PHENYL-PYRIMIDINE LIQUID CRYSTAL COMPOUNDS AND LIQUID CRYSTAL COMPOSITIONS CONTAINING THE SAME

[75] Inventors: Ryoichi Higuchi; Takao Sakurai; Tadahiko Yokota; Naoko Mikami; Eri Yamamoto; Koji Takeuchi, all of Kawasaki, Japan

[73] Assignee: Ajinomoto Co., Inc., Tokyo, Japan

[21] Appl. No.: 176,154

[22] Filed: Mar. 31, 1988

[30] Foreign Application Priority Data

Mar. 31, 1987 [JP] Japan .................................. 62-78289
Oct. 29, 1987 [JP] Japan .................................. 62-274389

[51] Int. Cl.$^4$ ...................... G02F 1/13; C09K 19/34; C07D 239/02
[52] U.S. Cl. .......................... 252/299.61; 252/299.01; 350/350 R; 350/350 S; 544/298; 544/335
[58] Field of Search ...................... 252/299.61, 299.01; 350/350 R, 350 S; 544/298, 335

[56] References Cited

U.S. PATENT DOCUMENTS

| | | | |
|---|---|---|---|
| 4,311,610 | 1/1982 | Zaschke et al. | 252/299.61 |
| 4,348,298 | 9/1982 | Zaschke et al. | 252/299.61 |
| 4,647,398 | 3/1987 | Saito et al. | 252/299.01 |
| 4,697,015 | 9/1987 | Kano et al. | 252/299.61 |
| 4,725,688 | 2/1988 | Taguchi et al. | 252/299.61 |
| 4,728,458 | 3/1988 | Higuchi et al. | 252/299.01 |
| 4,732,699 | 3/1988 | Higuchi et al. | 252/299.01 |
| 4,752,413 | 6/1988 | Inoue et al. | 252/299.61 |
| 4,759,869 | 7/1988 | Ohno et al. | 252/299.01 |
| 4,765,924 | 8/1988 | Inoue et al. | 252/299.61 |
| 4,775,223 | 10/1988 | Yoshinaga et al. | 252/299.61 |

FOREIGN PATENT DOCUMENTS

| | | | |
|---|---|---|---|
| 206228 | 12/1986 | European Pat. Off. | 252/299.61 |
| 225195 | 6/1987 | European Pat. Off. | 252/299.61 |
| 247804 | 12/1987 | European Pat. Off. | 252/299.61 |
| 2257588 | 6/1973 | Fed. Rep. of Germany | 252/299.61 |
| 3518734 | 11/1986 | Fed. Rep. of Germany | 252/299.61 |
| 159505 | 3/1983 | German Democratic Rep. | 252/299.61 |
| 2049692 | 12/1980 | United Kingdom | 252/299.61 |
| 86/06401 | 11/1966 | World Int. Prop. O. | 252/299.61 |

*Primary Examiner*—Teddy S. Gron
*Attorney, Agent, or Firm*—Oblon, Spivak, McClelland, Maier & Neustadt

[57] ABSTRACT

A phenyl-pyrimidine liquid crystal compound represented by the formula:

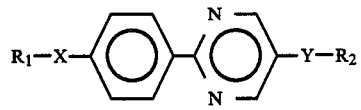

wherein $R_1$ and $R_2$ are the same or different and each represent an alkyl group having 1 to 18 carbon atoms, and X and Y each represent one of a single bond, —O—, —OCO—, —COO— and —OCOO—, provided that one of X and Y is —OCOO—.

15 Claims, No Drawings

PHENYL-PYRIMIDINE LIQUID CRYSTAL COMPOUNDS AND LIQUID CRYSTAL COMPOSITIONS CONTAINING THE SAME

BACKGROUND OF THE INVENTION

1. Field of the Invention

The present invention relates to liquid crystal compounds and liquid crystal compositions containing the same.

2. Description of the Background

Display modes of liquid crystal display elements now widely in use are those of the twist nematic type (TN type) and dynamic scattering type (DS type). These modes are display modes with nematic liquid crystal cells containing nematic liquid crystals as a main component. The conventional nematic liquid crystal cells are disadvantageous in that the response speed is so slow that a response speed only of the order of several m sec is obtained at most. This drawback greatly narrows the applicable range of nematic crystal cells. However, it has recently been recognized that by using smectic liquid cells, higher response speeds are possible.

Some optically active smectic liquid crystals are known to exhibit a strong dielectric property. Examples of liquid crystals exhibiting a strong dielectric property, are representative compounds such as 4-(4-n-decyloxybenzylideneamino) cinnamic acid-2-methyl butyl ester (hereinafter abridged as DOBAMBC) as synthesized by R. B. Meyer et al. in 1975. These compounds are characterized by exhibiting a strong dielectric property in the chiral smectic C phase (J. Physique, 36, L-69 (1975).

Recently, a high speed response of $\mu$ sec order has been found in a thin film cell of DOBAMBC by N. A. Clark et al. (Appl. Phys. Lett. 36, 89 (1980)). Thereafter, strongly dielectric liquid crystals have been studied due to their high speed response as a material usable not only for displays such as liquid crystal televisions but also as a raw material for optoelectronics and related devices such as light printer heads, optical Fourier transform devices and light values.

Display devices using strongly dielectric liquid crystals can produce printing with short pulses, thus making memorization thereof possible, and thus also making it possible to easily produce large areas of display.

Unfortunately, display devices using a strongly dielectric crystal composition are not yet practicable due to the fact that the response speed of the composition is inadequate and the usable temperature range is prohibitively narrow. Thus, a need continues to exist for a strongly dielectric liquid crystal composition which has a high response speed over a wide range of temperature.

SUMMARY OF THE INVENTION

It is an object of the present invention to provide liquid crystal compounds and compositions containing the same which exhibit a high response speed.

It is also an object of this invention to provide such compounds and compositions exhibiting a high response speed over a wide range of temperatures.

Further, it is an object of the present invention to provide a display cell containing the above liquid crystal compounds and compositions.

BRIEF DESCRIPTION OF THE DRAWING

FIG. 1 shows the infrared absorption spectrum by the Nujol method of 2-(4-decyloxyphenyl)-5-octyloxycarbonyloxypyrimidine as obtained in Example 1.

DESCRIPTION OF THE PREFERRED EMBODIMENTS

The present invention provides phenyl-pyrimidine liquid crystal compounds of the formula:

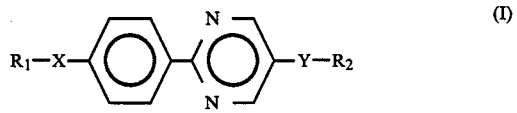

(I)

wherein $R_1$ and $R_2$ each represent an alkyl group having 1 to about 18 carbon atoms, and X and Y each represent one of a single bond, —O—, —OCO—, —COO— and —OCOO—, provided that one of X and Y is always —OCOO—, and liquid crystal compositions containing the same.

The present invention also provides a strongly dielectric liquid crystal composition having a high response speed over a wide range of temperature, containing one or more compounds of the present invention and one or more chiral smectic C liquid crystal compounds, or mixtures of the compounds of the present invention and a chiral smectic C liquid crystal composition.

The compounds of the formula (I) may be synthesized as follows.

A 5-hydroxypyrimidine derivative represented by the formula (a):

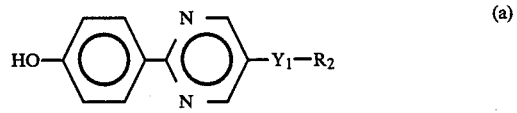

(a)

where $R_2$ represents an alkyl group having 1 to about 18 carbon atoms, and $Y_1$ represents one of a single bond, —O—, —OCO— and —COO—; or a 5-hydroxypyrimidine derivative represented by the formula (b):

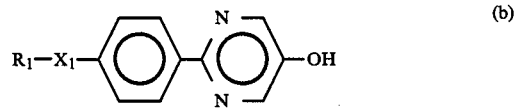

(b)

wherein $R_1$ represents an alkyl group having 1 to about 18 carbon atoms, $X_1$ represents a single bond, —O—, —OCO— and —COO—; is reacted with a chlorocarboxylic acid alkyl ester represented by the formula (c):

R₃—OCOCl (c)

wherein $R_3$ represents an alkyl group having 1 to about 18 carbon atoms in the presence of a base such as pyridine or triethylamine in an inert solvent such as carbon tetrachloride or chloroform followed by purification to obtain a desired product.

A strongly dielectric liquid crystal composition having a high response speed over a wide range of temperature may be obtained by mixing one or more of the compounds of the present invention with one or more chiral smectic C liquid crystal compounds or with a chiral smectic C liquid crystal composition.

For example, a strongly dielectric liquid crystal composition such as the mixture comprising

| | |
|---|---|
| (S,S)—1-chloro-2-methylbutylcarboxylic acid 4-(4-octyloxyphenyl)phenyl ester | 39.0 wt. % |
| (S,S)—1-chloro-2-methylbutylcarboxylic acid 4-(4-nonyloxycarbonyloxyphenyl)phenyl ester | 22.0 wt. % |
| (S)—1-chloro-2-methylpropylcarboxylic acid 4-(4-nonyloxycarbonyloxyphenyl)phenyl ester | 20.0 wt. % |
| (S,S)—1-chloro-2-methylbutylcarboxylic acid 4-(4-nonylcarbonyloxyphenyl)phenyl ester | 19.0 wt. % | exhibits a chiral smectic C phase only in a narrow temperature range of 38° to 60° C. However, a strongly dielectric liquid crystal composition which is the mixture of this composition with a compound of the present invention, 2-(4-nonyloxycarbonyloxyphenyl)-5-dodecylpyrimidine in the ratio of 5:35 exhibits a chiral smectic C phase over a wide temperature range of room temperature to 63.0° C., and also has a very high response speed of 34 μS.

The present invention will now be further illustrated by the following Examples which are provided for purposes of illustration only and are not intended to limit the present invention.

EXAMPLE 1

Synthesis and evaluation of 2-(4-decyloxyphenyl)-5-octyloxycarbonyloxypyrimidine (A):

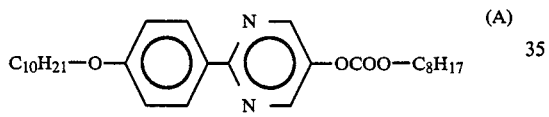

Ethyl benzyloxyacetate (B) was obtained by esterifying benzyloxyacetic acid as obtained from benzyl alcohol and chloroacetic acid by a conventional Williamson synthesis. (B) (9.7 g) and 3.7 g of ethyl formate were dissolved in 25 ml of ether, and stirred in the presence of sodium for 2 hours, and ether was distilled away to obtain sodium 2-benzyloxy-2-ethoxycarbonylethylenolate (C). To this compound was added a solution as prepared by dissolving 14.2 g of 4-decyloxybenzamidine hydrochloride (synthesized from 4-decyloxycyanobenzene by a conventional method) in 80 ml of ethanol and adding 1.2 g of sodium, and the mixture was refluxed for 2 hours. The solvent was distilled away to obtained 2-(4-octyloxyphenyl)-4-hydroxy-5-benzyloxypyrimidine (D). (D) (2 g) together with phosphorus oxychloride was refluxed for 3 hours to obtain 2-(4-octyloxyphenyl)-4-chloro-5-benzyloxypyrimidine (E).

(E) (1.7 g) was hydrogenated in the presence of Pd-C and potassium carbonate in 1,4-dioxane at normal pressure to yield 2-(4-octyloxyphenyl)-5-hydroxypyrimidine (F). (F) (1.0 g) was dissolved in 50 ml of carbon tetrachloride. 0.8 ml of octyl chlorocarboxylate and 5 ml of pyridine were added, and the mixture was stirred for a while and then allowed to stand overnight. 1N hydrochloric acid was added thereto, and the carbon tetrachloride layer was taken and concentrated. The resulting residue was purified by repeated recrystallization from methanol to obtain 2-(4-decyloxyphenyl)-5-octyloxycarbonyloxypyrimidine (A).

The IR-spectrum of this compound is shown in FIG. 1.

The phase transition point of this compound is shown in Table 1.

EXAMPLE 2

Various 2-(4-alkyloxyphenyl)-5-alkyloxycarbonyloxypyrimidines were synthesized from various 2-(4-alkyloxyphenyl)-5-hydroxypyrimidines according to the method described in Example 1 and various chlorocarboxylic acid alkyl esters according to the method described in Example 1.

The phase transition point of the resulting compounds is shown in Table 1.

EXAMPLE 3

Synthesis and evaluation of 2-(4-nonyloxycarbonyloxyphenyl)-5-dodecylpyrmidine (H)

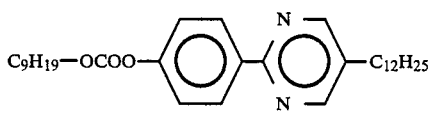

2-(4-Hydroxyphenyl)-5-dodecylpyrimidine (G) (1.0 g) was dissolved in 50 ml of carbon tetrachloride, 0.8 ml of nonyl chlorocarboxylate and 5 ml of pyridine were added, and the mixture was stirred for a while and allowed to stand overnight. 1N Hydrochloric acid was added, and the carbon tetrachloride layer was taken and concentrated. The residue was purified by repeated recrystallization from methanol to obtain (H).

EXAMPLE 4

Various 2-(4-alkyloxycarbonyloxyphenyl)-5-alkylpyrimidine compounds were synthesized from various 2-(4-hydroxyphenyl)-5-alkylpyrimidine compounds and various chlorocarboxylic acid alkyl esters according to the same method as described in Example 3.

The phase transition point of the resulting compounds is shown in Table 1.

EXAMPLE 5

A chiral smectic C liquid crystal composition having the following composition was prepared:

| | |
|---|---|
| (S,S)—1-chloro-2-methylbutylcarboxylic acid 4-(4-octyloxyphenyl)phenyl ester | 25.4 wt. % |
| (S,S)—1-chloro-2-methylbutylacrboxylic acid 4-(4-nonyloxycarbonyloxyphenyl)phenyl ester | 14.3 wt. % |
| (S)—1-chloro-2-methylpropylcarboxylic acid 4-(4-nonyloxycarbonyloxyphenyl)phenyl ester | 13.0 wt. % |
| (S,S)—1-chloro-2-methylbutylcarboxylic acid 4-(4-nonylcarbonyloxyphenyl)phenyl ester | 12.4 wt. % |
| 2-(4-nonyloxycarbonyloxyphenyl)-5-dodecylpyrimidine | 35.0 wt. % |

This composition exhibited a chiral smectic C phase over a temperature range of from room temperature to 63° C., a smectic A phase over a temperature range of from 63° C. to 66° C. and an isotropic phase at a temperature of 66° C. or more.

The response speed of the composition as determined by encapsulating it into a cell of 2.7 μm which had been subjected to an orientation treatment with a polyimide and exposing it to a rectangular wave of ±40 V was 34 μS at 25° C.

EXAMPLE 6

A chiral smectic C liquid crystal composition having the following composition was prepared:

| | |
|---|---|
| (S,S)—1-chloro-2-methylbutylcarboxylic acid 4-(4-octyloxyphenyl)phenyl ester | 26.5 wt. % |
| (S,S)—1-chloro-2-methylbutylcarboxylic acid 4-(4-nonyloxycarbonyloxyphenyl)phenyl ester | 15.0 wt. % |
| (S)—1-chloro-2-methylpropylcarboxylic acid 4-(4-nonyloxycarbonyloxyphenyl)phenyl ester | 13.6 wt. % |
| (S,S)—1-chloro-2-methylbutylcarboxylic acid 4-(4-nonyloxycarbonyloxyphenyl)pnenyl ester | 12.9 wt. % |
| 2-(4-decyloxyphenyl-5-octyloxycarbonyloxypyrimidine | 32.0 wt. % |

This composition exhibited a chiral smectic C phase over a temperature range of from room temperature to 58° C., a smectic A phase over a temperature range of from 58° C. to 60° C., and an isotropic phase at a temperature of 60° C. or more.

The response speed of the composition as determined by encapsulating it into a cell of 3.3 μm which had been subjected to an orientation treatment with a polyimide and exposing it to a rectangular wave of ±40 V was 20 μS at 25° C.

EXAMPLE 7

A chiral smectic C liquid crystal composition having the following composition was prepared:

| | |
|---|---|
| (S,S)—1-chloro-2-methylbutylcarboxylic acid 4-(4-octyloxyphenyl)phenyl ester | 10.7 wt. % |
| (S,S)—1-chloro-2-methylbutylcarboxylic acid 4-(4-nonyloxycarbonyloxyphenyl)phenyl ester | 7.3 wt. % |
| (R)-4-(4-nonylcarbonyloxyphenyl)benzoic acid 2-chloro-3-methylbutyl ester | 19.5 wt. % |
| 2-(4-nonyloxyphenyl)-5-nonylpyrimidine | 12.5 wt. % |
| 2-(4-octyloxyphenyl)-5-octylpyrimidine | 12.5 wt. % |
| 2-(4-octyloxyphenyl)-5-nonylpyrimidine | 2.5 wt. % |
| 2-(4-decyloxyphenyl)-5-octyloxycarbonyloxypyrimidine | 12.5 wt. % |
| 2-(4-nonyloxycarbonyloxyphenyl)-5-dodecylpyrimidine | 12.5 wt. % |

This composition exhibited a chiral smectic C phase over a temperature rang of from below freezing to 41° C., a smectic A phase over a temperature range of from 41° C. to 61° C., and an isotropic phase at a temperature of 61° C. or more.

The response speed of the composition as determined by encapsulating it into a cell of 3.3 μm which had been subjected to an orientation treatment with a polyimide and exposing it to a rectangular wave of ±10 V was 24 μS at 23° C.

EXAMPLE 8

A chiral smectic C liquid crystal composition having the following composition was prepared:

| | |
|---|---|
| (S,S)—1-chloro-2-methylbutylcarboxylic acid 4-(4-octyloxyphenyl)phenyl ester | 10.8 wt. % |
| (S,S)—1-chloro-2-methylbutylcarboxylic acid 4-(4-nonyloxycarbonyloxyphenyl)phenyl ester | 7.4 wt. % |
| (R)-4-(4-nonylcarbonyloxyphenyl)benzoic acid 2-chloro-3-methylbutyl ester | 20.0 wt. % |
| 2-(4-nonyloxyphenyl)-5-nonylpyrimidine | 12.7 wt. % |
| 2-(4-octyloxyphenyl)-5-octylpyrimidine | 12.7 wt. % |
| 2-(4-octyloxyphenyl)-5-nonylpyrimidine | 12.7 wt. % |
| 2-(4-decyloxyphenyl)-5-octyloxycarbonyloxypyrimidine | 6.6 wt. % |
| 2-(4-decyloxyphenyl)-5-pentyloxycarbonyloxypyrimidine | 3.9 wt. % |
| 2-(4-nonyloxycarbonyloxyphenyl)-5-heptylpyrimidine | 3.3 wt. % |
| 2-(4-nonyloxycarbonyloxyphenyl)-5-dodecylpyrimidine | 4.9 wt. % |
| 2-(4-pentyloxycarbonyloxyphenyl)-5-dodecylpyrimidine | 5.0 wt. % |

This composition exhibited a chiral smectic C phase over a temperature range of from below freezing point to 35° C., a smectic A phase over a temperature range of from 35° C. to 59° C., and an isotropic phase at a temperature of 59° C. or more.

The response speed of the composition as determined by encapsulating it into a cell of 3.3 μm which had been subjected to an orientation treatment with a polyimide and exposing it to a rectangular wave of ±10 V was 18 μS at 23° C.

Having now fully described the present invention, it will be apparent to one of ordinary skill in the art that many changes and modifications can be made thereto without departing from the spirit or scope of the invention as set forth herein.

TABLE 1

Phasetransfer temperature of the compound

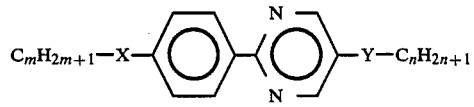

| m | n | —X— | —Y— | C | SC | SA | N | I |
|---|---|---|---|---|---|---|---|---|
| 7 | 11 | —O— | —OCOO— | ● | 77● | | ● | 85● |
| 7 | 12 | —O— | —OCOO— | ● | 78● | | ● | 85● |
| 8 | 6 | —O— | —OCOO— | ● | 66 | | ● | 77● |
| 8 | 7 | —O— | —OCOO— | ● | 74 | | ● | 80● |
| 8 | 8 | —O— | —OCOO— | ● | 71● | 72 | ● | 83● |
| 8 | 9 | —O— | —OCOO— | ● | 67● | 79 | ● | 84● |
| 8 | 12 | —O— | —OCOO— | ● | 80 | | ● | 89● |
| 10 | 5 | —O— | —OCOO— | ● | 56 | | ● | 73● |
| 10 | 6 | —O— | —OCOO— | ● | 72 | | ● | 73● |
| 10 | 7 | —O— | —OCOO— | ● | 72 | | ● | 80● |
| 10 | 8 | —O— | —OCOO— | ● | 68● | | 75● | 84● |
| 10 | 12 | —O— | —OCOO— | ● | 74● | | ● | 90● |
| 5 | 12 | —OCOO— | — | ● | 48 | ● | | 52● |
| 9 | 7 | —OCOO— | — | ● | 48 | | | ● |
| 9 | 12 | —OCOO— | — | ● | 46● | | | 59● |
| 11 | 9 | —OCOO— | — | ● | 53 | | ● | 55● |
| 12 | 12 | —OCOO— | — | ● | 57● | | | 60● |

What is claimed as new and desired to be secured by Letters Patent of the United States is:

1. A compound of the formula:

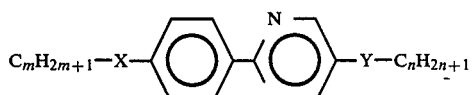

wherein either X is —O—, Y is —OCOO—, m is 7–10 and n is 5–12; or X is —OCOO—, Y is a direct bond, m is 5–12 and n is 7–12.

2. The compound of claim 1, wherein Y is a direct bond.

3. The compound of claim 1, wherein X is —O—.

4. A liquid crystal composition having at least two components, one of which is one or more compounds of the formula:

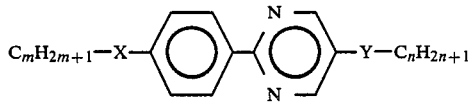

wherein either X is —O—, Y is —OCOO—, m is 7-10 and n is 5-12; or X is —OCOO—, Y is a direct bond, m is 5-12 and n is 7-12.

5. The liquid crystal composition of claim 4, wherein Y is a direct bond.

6. The liquid crystal composition of claim 4, wherein X is —O—.

7. The compound of claim 1, wherein when X is —O—, and Y is —OCOO—, m has a value 7, 8 and 10 and n has a value of 5, 6, 7, 8, 9, 11 and 12; and when X is —OCOO—, and Y is a direct bond, m has a value of 5, 9, 11 and 12 and n has a value of 7, 9 and 12.

8. A liquid crystal composition, comprising one or more chiral smectic C liquid crystal compounds, and one or more other compounds of the formula:

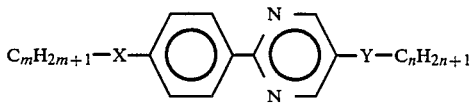

wherein either X is —O—, Y is —OCOO—, m is 7-10 and n is 5-12; or X is —OCOO—, Y is a direct bond, m is 5-12 and n is 7-12.

9. The liquid crystal composition of claim 8, wherein Y is a direct bond.

10. The liquid crystal composition of claim 8, wherein X is —O—.

11. A liquid crystal display cell containing one or more of the compounds of claim 1.

12. A liquid crystal display cell containing one or more of the compounds of claim 2.

13. A liquid crystal display cell containing one or more of the compounds of claim 3.

14. A liquid crystal display cell containing the liquid crystal composition of claim 4.

15. A liquid crytal display cell containing the liquid crystal composition of claim 8.

* * * * *